(12) United States Patent
Nakamura (10) Patent No.: US 8,200,073 B1
(45) Date of Patent: Jun. 12, 2012

(54) DENTAL TREATMENT OBSERVATION SYSTEM

(75) Inventor: Katsushige Nakamura, Chofu (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 0 days.

(21) Appl. No.: 13/011,110

(22) Filed: Jan. 21, 2011

(51) Int. Cl.
*A61B 1/04* (2006.01)

(52) U.S. Cl. ............... 396/16; 348/66; 248/324

(58) Field of Classification Search ............ 396/16, 396/14; 359/368, 376; 348/66, 79; 248/324
See application file for complete search history.

(56) References Cited

U.S. PATENT DOCUMENTS

| | | | |
|---|---|---|---|
| 5,825,536 A | * | 10/1998 | Yasunaga et al. ............ 359/384 |
| 2004/0036962 A1 | | 2/2004 | Brunner et al. |
| 2007/0080275 A1 | * | 4/2007 | Stachowski et al. ......... 248/323 |
| 2009/0047617 A1 | * | 2/2009 | Bush et al. ..................... 433/28 |

FOREIGN PATENT DOCUMENTS

JP 2607828 5/1997

* cited by examiner

*Primary Examiner* — Christopher Mahoney
(74) *Attorney, Agent, or Firm* — Greenblum & Bernstein P.L.C.

(57) ABSTRACT

A dental treatment observation system includes a photographing unit supported with a first auxiliary arm at a front end of a support arm extending from a stand and a stereoscopic display unit supported with a second auxiliary arm at the front end of the support arm. The stand allows the photographing unit and stereoscopic display unit together to be widely moved and the first and second auxiliary arms allow the units to be separately moved in optional directions. The system is appropriate for dental treatment and is capable of reducing fatigue of a dentist during treatment.

5 Claims, 8 Drawing Sheets

DENTAL TREATMENT OBSERVATION SYSTEM

BACKGROUND OF THE INVENTION

1. Field of the Invention

The present invention relates to a dental treatment observation system.

2. Description of Related Art

For surgery, US Patent Application Publication No. 2004/0036962 discloses an observation system that photographs a surgical site with a camera, displays the photographed image on a display unit separately supported from the camera, and allows an operator to observe the displayed image. Since the camera and display unit are separated from each other, the operator can observe the image with eyepieces in a comfortable posture and naturally conduct surgery without fatigue.

SUMMARY OF THE INVENTION

The above-mentioned related art may be appropriate for surgery but is not applicable as it is to dental treatment. This is because the surgery has no need of widely moving the camera during surgery but the dental treatment needs to widely move the camera whenever the patient rinses his or her mouth. In addition, the surgery needs no frequent change of orientation of the camera. On the other hand, the dental treatment needs frequent change of orientation of the camera in order to observe a treating site from various directions.

To meet the needs of dental treatment, the present invention provides a dental treatment observation system appropriate for the dental treatment.

According to an aspect of the present invention, the dental treatment observation system includes a photographing unit movably and rotatably supported with a first auxiliary arm at a front end of a support arm extending from a stand, the photographing unit stereoscopically photographing an object and providing a pair of left and right images of the object having a binocular parallax and a stereoscopic display unit movably and rotatably supported with a second auxiliary arm at the front end of the support arm, the stereoscopic display unit displaying the pair of left and right images on internal display panels so that the images are stereoscopically observed through a pair of eyepieces.

According to another aspect of the present invention, the dental treatment observation system includes a stand having a parallel linkage provided with first and second parallel sub-linkages. The parallel linkage has first and second links that face each other and third and fourth links that face each other, the first link being supported by a stand body through a shaft, the fourth link supporting a counterweight, the third link being extended to form a support arm that supports a front link through a shaft. The first parallel sub-linkage has fifth and sixth links that face each other and seventh and eighth links that face each other, the fifth link being positionally fixed to the first link, the eighth link being positionally fixed to the stand body. The second parallel sub-linkage has four links including ninth and tenth links that face each other, the ninth link being positionally fixed to the seventh link, the tenth link being positionally fixed to the front link. The dental treatment observation system further includes a first auxiliary arm attached to the front link and configured to movably and rotatably support a photographing unit that stereoscopically photographs an object and provides a pair of left and right images of the object having a binocular parallax, the first auxiliary arm including third and fourth parallel sub-linkages. The third parallel sub-linkage has four links including eleventh and twelfth links that face each other, the eleventh link being positionally fixed to the front link. The fourth parallel sub-linkage has four links including thirteenth and fourteenth links that face each other, the thirteenth link being positionally fixed to the twelfth link, the photographing unit being positionally fixed to the fourteenth link. The dental treatment observation system also includes a second auxiliary arm attached to the front link and configured to movably and rotatably support a stereoscopic display unit that displays the pair of left and right images on internal display panels so that the images are stereoscopically observed through a pair of eyepieces, the second auxiliary arm including fifth and sixth parallel sub-linkages. The fifth parallel sub-linkage has four links including fifteenth and sixteenth links that face each other, the fifteenth link being positionally fixed to the front link. The sixth parallel sub-linkage has four links including seventeenth and eighteenth links that face each other, the seventeenth link being positionally fixed to the sixteenth link, the stereoscopic display unit being positionally fixed to the eighteenth link.

According to this aspect of the present invention, the eighth link of the first parallel sub-linkage positionally fixed to the stand body keeps a given angle relative to the front link that equivalently faces the eighth link through a torque transmission mechanism. The eleventh link of the first auxiliary arm positionally fixed to the front link keeps a given angle relative to the photographing unit that equivalently faces the eleventh link through a torque transmission mechanism. The seventeenth link of the second auxiliary arm positionally fixed to the front link keeps a given angle relative to the stereoscopic display unit that equivalently faces the seventeenth link through a torque transmission mechanism.

DESCRIPTION OF PREFERRED EMBODIMENTS

Figure 1:
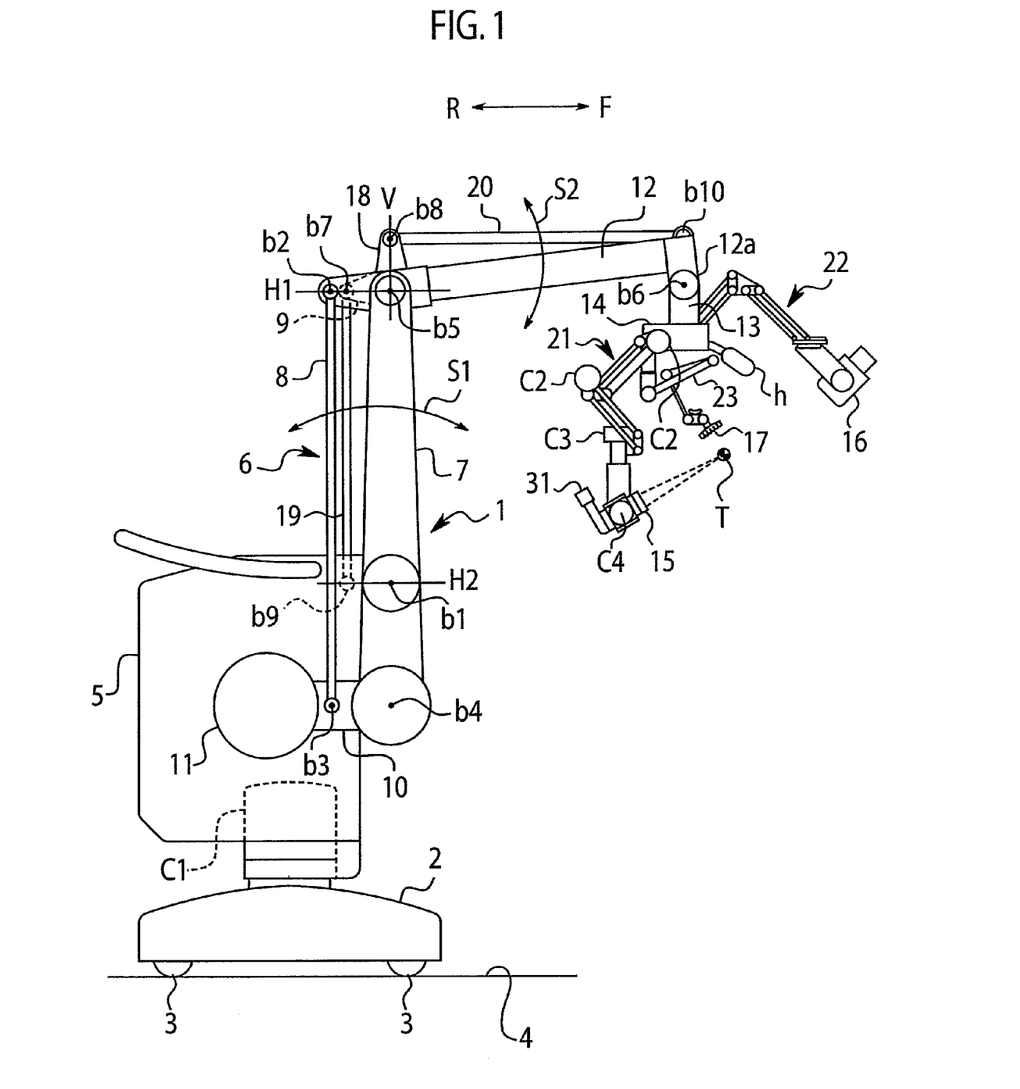
FIG. 1 is a side view generally illustrating a dental treatment observation system according to an embodiment of the present invention.

A dental treatment observation system according to an embodiment of the present invention will be explained with reference to FIGS. 1 to 8. In the following explanation, front side and rear side are defined with respect to the base 2 and are depicted by "F" and "R", respectively, as illustrated in FIG. 1.

A stand 1 has the base 2 whose bottom face has casters 3 provided with a locking mechanism. The casters 3 allow the stand 1 to move along a floor 4. On the base 2, a stand body 5 is installed. The stand body 5 is horizontally rotatable on the base 2. Rotation of the stand body 5 is locked and released with an electromagnetic clutch C1.

A rotation axis point b1 is set at an upper front end of the stand body 5, to support a parallel linkage 6. The parallel linkage 6 includes two longitudinal links 7 and 8 that are parallel to each other and two lateral links 9 and 10 that are parallel to each other. The links 7 to 10 are joined together through connection axis points b2, b3, b4, and b5. A lower intermediate part of the longitudinal link 7 on the front side of the parallel linkage 6 is supported at the rotation axis point b1. The rotation axis point b1 is provided with an electromagnetic clutch to lock and release rotation of the longitudinal link 7 in a direction S1. A rear end of the lower lateral link 10 is provided with a counterweight 11.

The upper lateral link 9 of the parallel linkage 6 is extended toward the front side, to integrally form a support arm 12. A front end 12a of the support arm 12 is downwardly bent. The dependent front end 12a is connected through a connection axis point b6 to a vertical front link 13 that is rotatable around the connection axis point b6. Since the front end 12a is downwardly bent, the support arm 12 upwardly inclines toward the front side. In connection with a load weight balance, the rotation axis point b1 serves as a fulcrum and the connection axis point b6 as a point of action. The connection axis point b6 is positionally fixed to the upper lateral link 9 defined by the connection axis points b2 and b5.

A lower part of the front link 13 is provided with a support box 14 that is horizontally rotatable and supports a photographing unit 15, a stereoscopic display unit 16, and an LED light 17. The supporting of the photographing unit 15 and the like will be explained in detail later.

The connection axis point b5 serving as a start point of the support arm 12 supports through a shaft an L-shaped crank 18 serving as an angular position transformer of link element. The crank 18 includes a horizontal axis point b7 positioned on a horizontal line H1 on which the connection axis point b5 is present and a vertical axis point b8 positioned on a vertical (plumb) line V on which the connection axis point b5 is present. The crank 18 positionally fixes the link elements b7-b5 and b8-b5 with respect to each other and acts as the angular position transformer of these link elements.

The horizontal axis point b7 is connected through a link 19 to a connection axis point b9 that is set on the stand body 5 and is positioned on a horizontal line H2 on which the rotation axis point b1 is present. A link element fixed to the link 19 and defined by the rotation axis points b7 and b9 and a link element fixed to the longitudinal link 7 and defined by the rotation axis points b5 and b1 are parallel with each other and they have the same lengths. The rotation axis points b7, b5, b1, and b9 define a first parallel sub-linkage that commonly employs the longitudinal link 7 with the parallel linkage 6.

The vertical axis point b8 of the crank 18 is connected through a link 20 to a connection axis point b10 that is at an upper end of the front link 13. The link 20 includes a link element defined by the axis points b8 and b10 which is in parallel with a link element fixed to the support arm 12 that is defined by the axis points b5 and b6. The link element fixed to the link 20 has the same length as that of the support arm 12. The axis points b5, b8, b10, and b6 define a second parallel sub-linkage.

The first and second parallel sub-linkages are connected to each other through the crank 18 as the angular position transformer of link element and deform within a virtual plane. Accordingly, the link b10-b6 to which the front link 13 is fixed and the link b1-b9 fixed to the stand body 5 serve as ends of a torque transmission mechanism consisting of the connected first and second parallel sub-linkages. Namely, an angle between the link b10-b6 and the link b1-b9 keeps a constant value and the link b10-b6 keeps a vertical/plumb state.

With the link 19, crank 18, and link 20, the crank 18 does not rotate even if the electromagnetic clutches of the stand 1 are released to turn the parallel linkage 6 around the rotation axis point b1 in the direction S1, or to turn the support arm 12 around the connection axis point b5 in a direction S2, or to simultaneously turn the parallel linkage 6 and support arm 12. Accordingly, the front link 13 always keeps vertical state.

A position maintaining mechanism with auxiliary arms will be explained.

Figure 2:
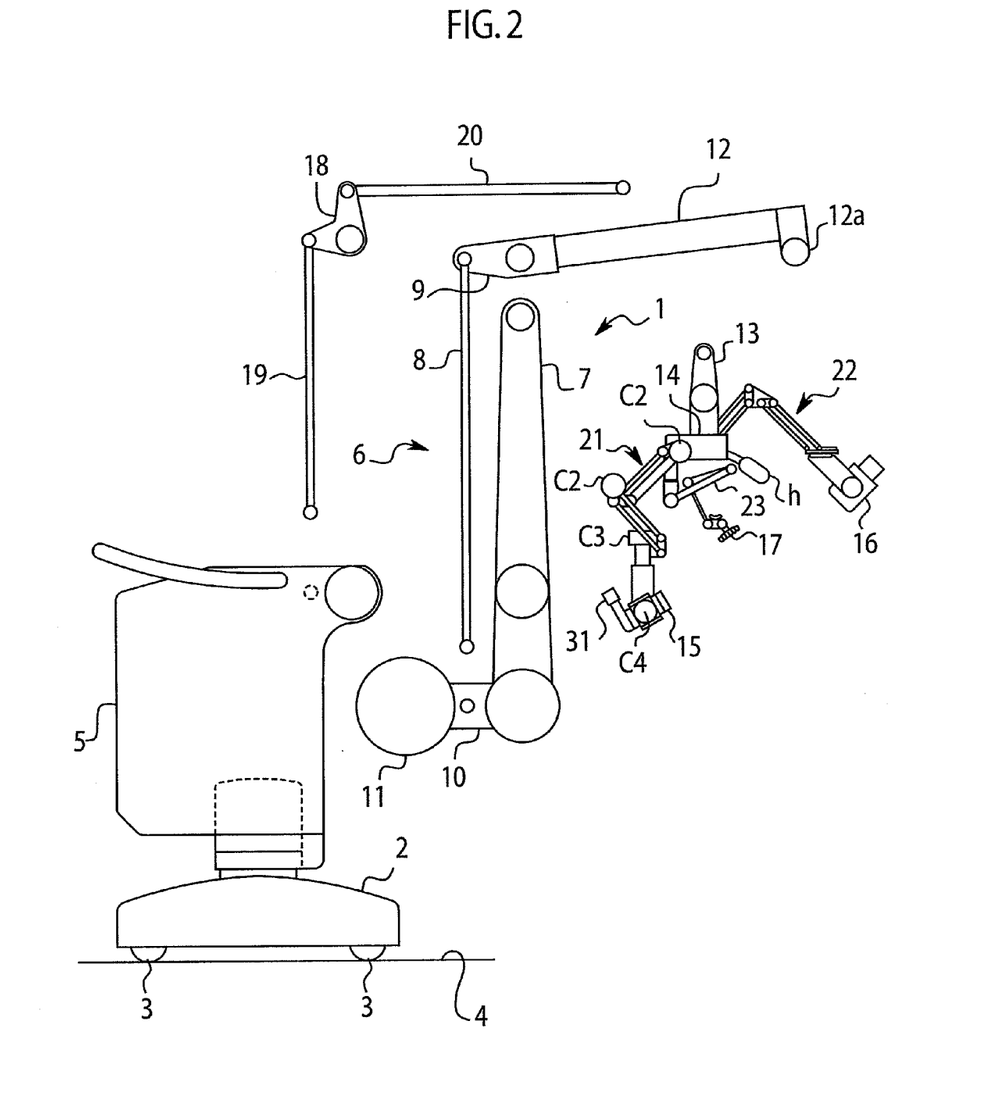
FIG. 2 is an exploded side view illustrating the dental treatment observation system.
Figure 3:
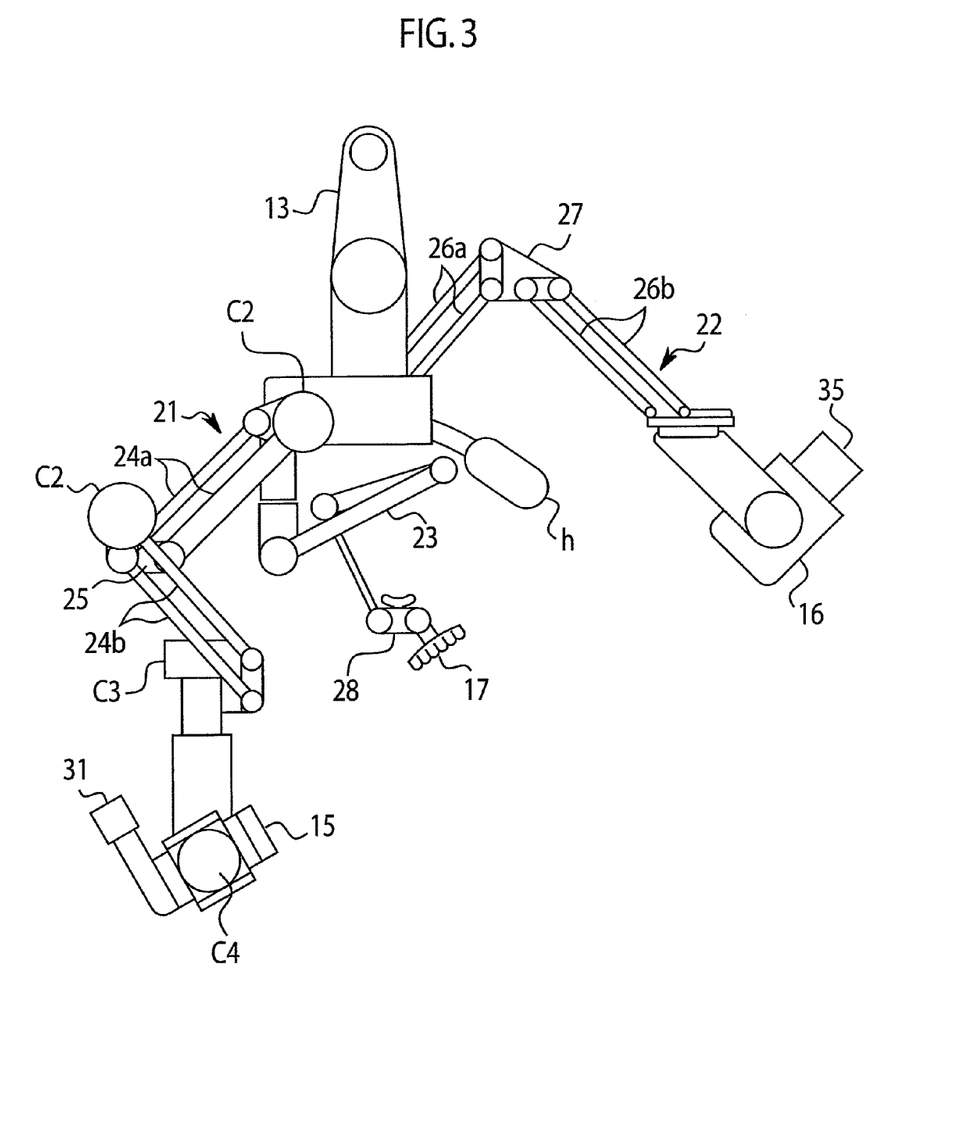
FIG. 3 is a side view illustrating a photographing unit and stereoscopic display unit supported with a front link of the dental treatment observation system.
Figure 4:
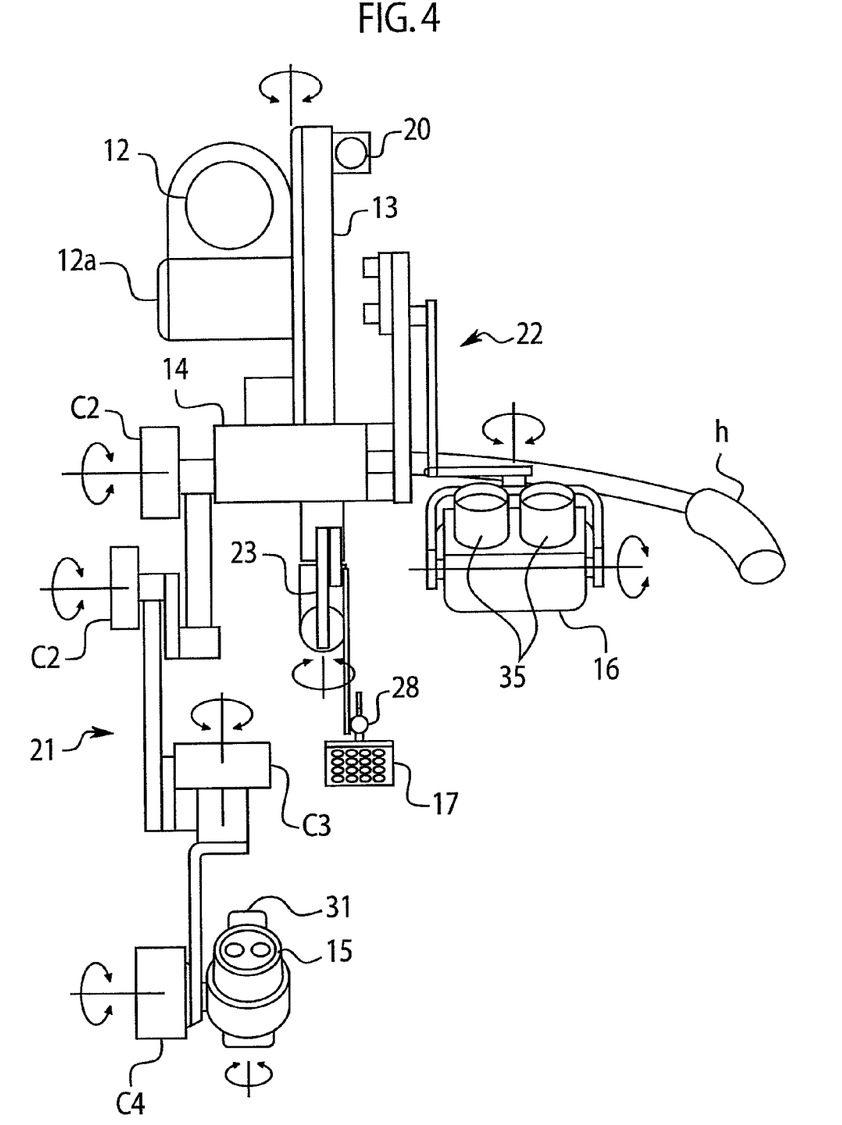
FIG. 4 is a front view illustrating the photographing unit and stereoscopic display unit supported with the front link.

As mentioned above, the front link 13 is always maintained its position in a vertical state and supports the support box 14. The support box 14 supports the photographing unit 15 through a first auxiliary arm 21, the stereoscopic display unit 16 through a second auxiliary arm 22, and the LED light 17 through a third auxiliary arm 23. The support box 14 has a handle h.

The first auxiliary arm 21 includes third and fourth parallel sub-linkages 24a and 24b that are connected to each other with a joint as an articulation 25 and are bent and stretched to move the photographing unit 15 serving as a load to a required spatial position. The second auxiliary arm 22 includes fifth and sixth parallel sub-linkages 26a and 26b that are connected to each other with a joint 27 as an articulation and are bent and stretched to move the stereoscopic display unit 16 as a load to a required spatial position.

Each of the third to sixth parallel sub-linkages includes four links. The third and fourth parallel sub-linkages 24a and 24b connected together with the joint 25 form the first auxiliary arm 21 and the fifth and sixth parallel sub-linkages 26a and 26b connected together with the joint 27 form the second auxiliary arm 22. The first and second auxiliary arms 21 and 22 each serve as a torque transmission mechanism. The joint 25 positionally fixes one link of the third parallel sub-linkage 24a on the front link 13 side to one link of the fourth parallel sub-linkage 24b on the photographing unit 15 side. In other words, the link element of the third parallel sub-linkage 24a is fixed relative to the link element of the fourth parallel sub-linkage 24b.

The joint 25 acts as an angular position transformer of link element configured to fix a relative angle between the two links at a predetermined angle as well as an articulation. More precisely, the joint 25 always maintains a fixed angle between the link of the third parallel sub-linkage 24a supported with the front link 13 and the link of the fourth parallel sub-linkage 24b supporting the photographing unit 15 at a constant angle. In each parallel sub-linkage, two opposing links are in parallel with each other. Two parallel sub-linkages are connected to each other through an angular position transformer of link element, i.e., a joint. In more detail, the link b9-b1 and link b10-b6 that is connected to the link opposing the link b9-b1 always keep a constant angle. The link of the third parallel sub-linkage 24a that is positionally fixed to the link b10-b6 and the link of the fourth parallel sub-linkage 24b that is connected to the opposing link of the just-mentioned link of the third parallel sub-linkage 24a keep a constant angle. The third and fourth parallel sub-linkages 24a and 24b deform through the joint 25 within a virtual plane containing the primary axis of the front link 13.

In the second auxiliary arm 22, the joint 27 connects the fifth parallel sub-linkage 26a on the front link 13 side to the sixth parallel sub-linkage 26b on the stereoscopic display unit 16 side. The joint 27 serves as an angular position transformer of link element configured to fix a relative angle between a link of the fifth parallel sub-linkage 26a and a link of the sixth parallel sub-linkage 26b at a predetermined angle as well as an articulation.

One link element of the third and fourth parallel sub-linkages 24a and 24b and one link element of the fifth and sixth parallel sub-linkages 26a and 26b are fixed relative to the front link 13 that is always vertical, and therefore, the photographing unit 15 and stereoscopic display unit 16 can maintain their postures even if they are moved relative to the front link 13.

The links fixed with the joint 25 (27) as an angular position transformer of link element keep a predetermined relative angle (right angle according to the embodiment), to effectively transfer torque when the photographing unit 15 (stereoscopic display unit 16) is moved in an optional direction. Namely, the photographing unit 15 (stereoscopic display unit 16) can keep a posture.

Although the torque transmission mechanism including the first parallel sub-linkage, crank 18, and second parallel sub-linkage deforms within a virtual plane, it works as a position maintaining mechanism to keep the front link 13 fixed to the second parallel sub-linkage in a constant posture (vertical) with respect to the stand body 5. Although the first auxiliary arm 21 deforms within a virtual plane, it works as a position maintaining mechanism to keep the photographing unit 15 in a provisional posture with respect to the primary axis of the front link 13. Although the second auxiliary arm 22 deforms within a virtual plane, it works as a position maintaining mechanism to keep the stereoscopic display unit 16 in a provisional posture with respect to the primary axis of the front link 13.

The first auxiliary arm 21 is provided with two electromagnetic clutches C2 for the third and fourth parallel sub-linkages 24a and 24b, respectively, to hold a position of the first auxiliary arm 21. The third parallel sub-linkage 24a on the front link 13 side has four connection axes. When one of the four connection axes is fixed by the clutch C2, two links connected to the connection axis are fixed to make the form of the third parallel sub-linkage 24a serving as a torque transmission mechanism fixed. Namely, to entirely fix the third parallel sub-linkage 24a, the clutch C2 may fix positions of two adjacent links at any one of the four connection axes. Similarly, the fourth parallel sub-linkage 24b on the photographing unit 15 side has four rotation axes. When one of the four rotation axes is fixed by the clutch C2, two links connected to the rotation axis are fixed to make the form of the fourth parallel sub-linkage 24b serving as a torque transmission mechanism fixed.

The second auxiliary arm 22 is provided with internal springs (not illustrated), so that the reactive force and friction of the internal springs may keep a position of the second auxiliary arm 22. The second auxiliary arm 22 includes the fifth parallel sub-linkage 26a on the front link 13 side and the sixth parallel sub-linkage 26b on the stereoscopic display unit 16 side. Each of the fifth and sixth parallel sub-linkages 26a and 26b is defined with four links. When adjacent links in any one of the sub-linkages 26a and 26b produce frictional force and the tension of the internal spring is applied to the links, the parallel sub-linkage restricts its free deformation and fixes its form.

The photographing unit 15 fixed to a front end of the first auxiliary arm 21 is horizontally rotatable. The stereoscopic display unit 16 fixed to a front end of the second auxiliary arm is horizontally rotatable. Horizontal rotation of the photographing unit 15 is restricted by an electromagnetic clutch C3 and vertical rotation of the photographing unit 15 is restricted by an electromagnetic clutch C4. The parts supported with the front link 13 are rotatable as indicated with arrows in FIG. 4. A rotation axis of the electromagnetic clutch C3 is always plumb due to the torque transmission mechanism between the link element b1-b9 and the link element b10-b6 and the first auxiliary arm 21, so that a view field will never incline when the photographing unit 15 is moved relative to the front link 13.

The third auxiliary arm 23 includes a plurality of arms supported through shafts and maintaining their states with friction. A front end of the third auxiliary arm 23 has a clamp 28 to hold a tool such as the LED light 17.

Figure 5:
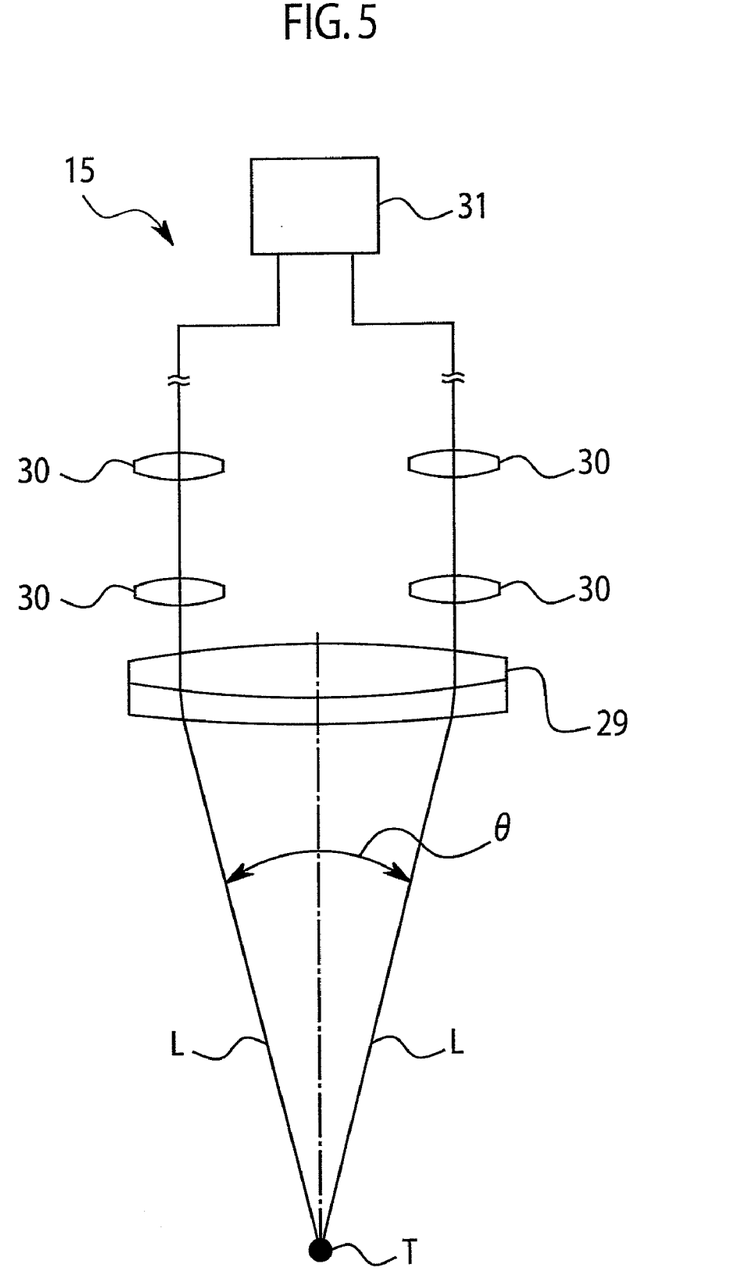
FIG. 5 is an explanatory view illustrating an optical system of the photographing unit.

The photographing unit 15 will be explained with reference to FIG. 5. The photographing unit 15 includes an objective lens 29 and zoom lenses 30. Light L having a predetermined convergence angle θ from a treatment target T is guided to and transmitted through the objective lens 29 and is divided into two systems corresponding to left and right eyes. The divided light beams pass through the left and right zoom lenses 30 and are guided through optical elements (not illustrated) such as prisms as disclosed in, for example, Japanese Patent No. 2607828 to a single photographing element (CCD image sensor) 31, which simultaneously photographs images for left and right eyes. The images photographed with the photographing unit 15 are observed with the stereoscopic display unit 16.

Figure 6:
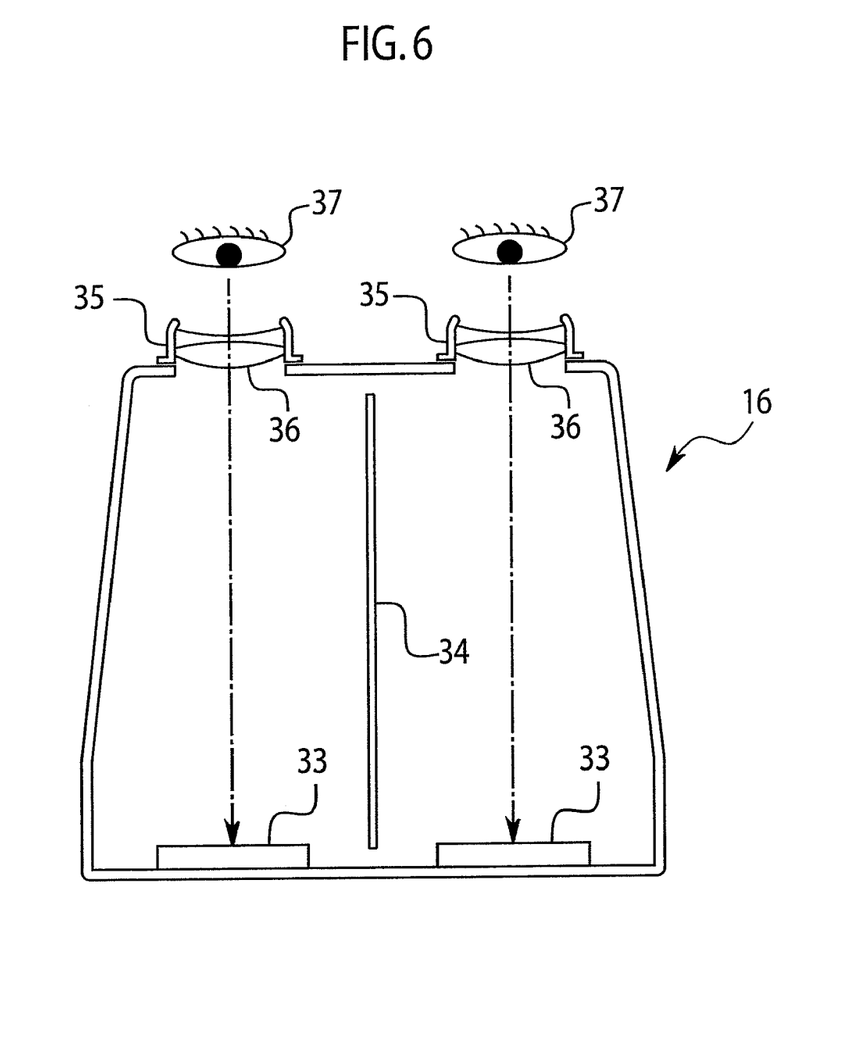
FIG. 6 is an explanatory view illustrating the stereoscopic display unit.

The stereoscopic display unit 16 illustrated in FIG. 6 has a case 32 incorporating a pair of display panels (small LCDs) 33 to display the electronic images of the target T photographed with the photographing unit 15 and having a binocular parallax. The case 32 has a partition 34 to define spaces for the display panels 33, respectively. The images displayed on the display panels 33 are observed through eyepiece lenses (magnifiers) 36 of eyepieces 35 by the eyes 37 of a dentist D. Consequently, the dentist D stereoscopically observes the treatment target T.

The total weight of the photographing unit 15, stereoscopic display unit 16, and the like suspended from the front link 13 is always balanced with the counterweight 11 about the rotation axis point b1 fixed at the stand body 5. When the electromagnetic clutches of the stand 1 are freed and the photographing unit 15 or the stereoscopic display unit 16 is moved with the hand of the dentist D to an optional position and when the hand is removed from the photographing unit 15 or the stereoscopic display unit 16 at the position, the photographing unit 15 or the stereoscopic display unit 16 stays at the position in the air because of the balancing achieved with the counterweight 11. Accordingly, the photographing unit 15 or the stereoscopic display unit 16 is easy to move.

The balanced state is kept even if any one of the first and second auxiliary arms 21 and 22 is bent to change the distance from the support box 14 to the photographing unit 15 or the stereoscopic display unit 16. Since the front link 13 is always vertical, no change occurs in the torque balance at the connection axis point b6 with respect to the rotation axis point b1 even if the photographing unit 15 is moved toward or away from the front link 13. Namely, the balanced state achieved with the counterweight 11 is kept without readjustment. Torque around the connection axis point b6 related to the first auxiliary arm 21, second auxiliary arm 22, and front link 13 is always compensated by the torque transmission mechanism between the link element b1-b9 and the link element b10-b6 that equivalently opposes the link element b1-b9.

The photographing unit 15 and stereoscopic display unit 16 are supported with the support box 14 at the front link 13 that is kept vertical. Accordingly, the photographing unit 15 and stereoscopic display unit 16 can be translated in vertical and horizontal directions by turning the parallel linkage 6 and support arm 12 without changing the posture and positional relationship of the units 15 and 16.

Figure 7:
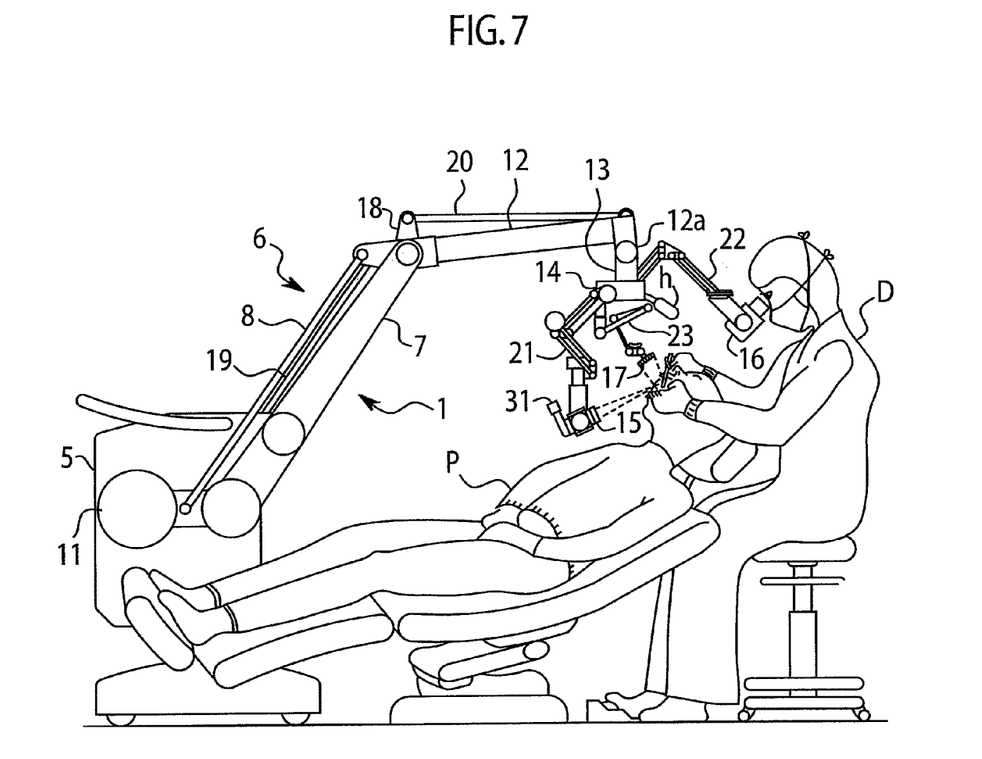
FIG. 7 is a view illustrating a using state of the dental treatment observation system.
Figure 8:
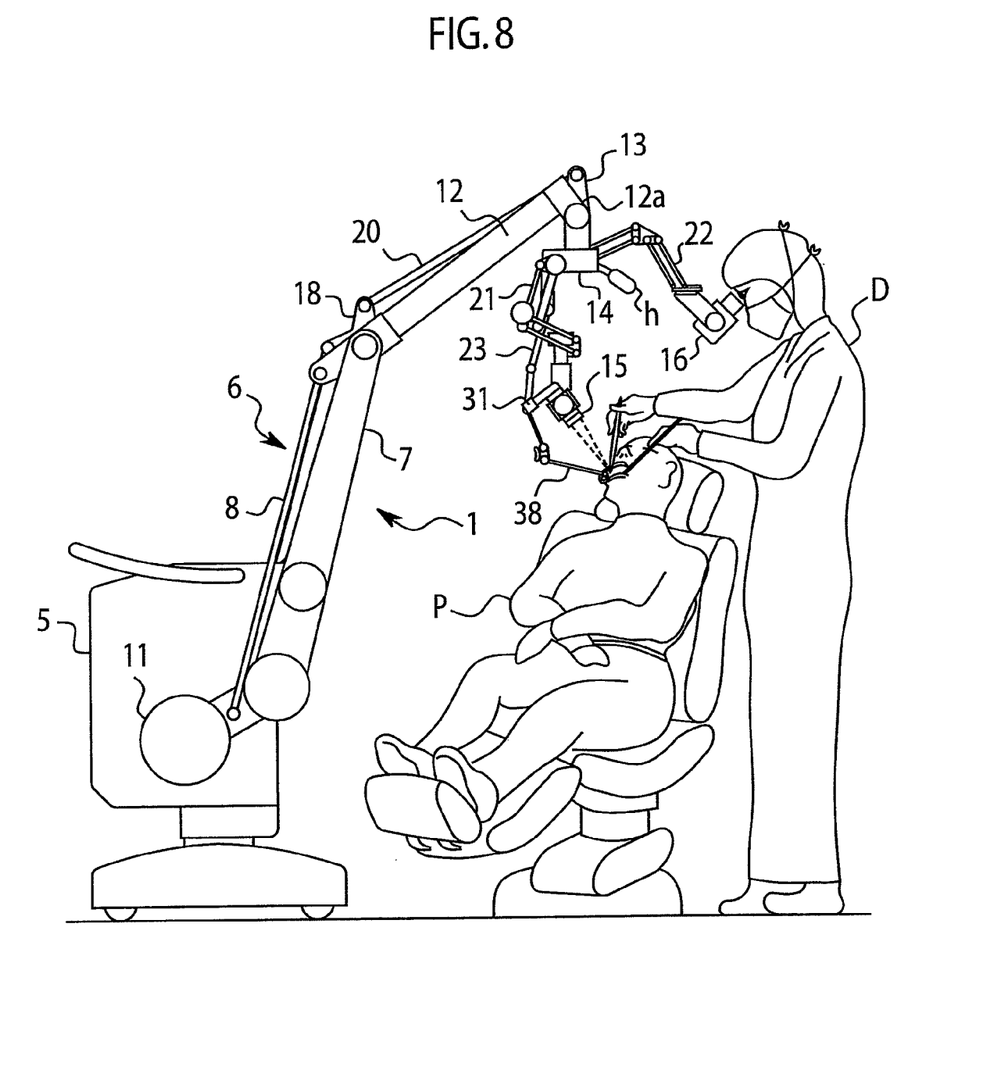
FIG. 8 is a view illustrating another using state of the dental treatment observation system.

Accordingly, the dental treatment observation system according to the embodiment can cope with a situation of FIG. 7 in which a patient P lies and a situation of FIG. 8 in which the patient P sits. In FIG. 8, the third auxiliary arm 23 holds a mirror 38 instead of the LED light 17.

The photographing unit 15 and stereoscopic display unit 16 are movable without changing the positional relationship thereof. For example, the units 15 and 16 are once moved away from the patient P, and if the unit 15 is again adjusted to the treatment target T, the unit 16 also moves to keep the positional relationship with the unit 15.

In addition, the photographing unit 15 and stereoscopic display unit 16 are separately movable with the first and second auxiliary arms 21 and 22, respectively. In this case, movement of one of the units 15 and 16 never affects the posture of the other. The dentist D, therefore, can photograph the treatment target T with the photographing unit 15 from an optional direction and can observe the photographed image with the stereoscopic display unit 16 at an optional position. This reduces fatigue of the dentist D during dental treatment.

Even when the first and second auxiliary arms 21 and 22 are optionally moved, the support arm 12 hardly interferes with the first and second auxiliary arms 21 and 22 because the front end 12a of the support arm 12 is downwardly bent so that the support arm 12 obliquely upwardly avoids the first and second auxiliary arms 21 and 22.

Images observed with the stereoscopic display unit 16 are photographed with the single photographing element 31 of the photographing unit 15, and therefore, a pair of left and right electronic images displayed on the display panels 33 of the stereoscopic display unit 16 are completely adjusted in characteristics such as colors, to realize clear stereoscopic observation. If the left and right images are photographed with left and right photographing elements, respectively, the images will minutely deviate from each other. If the dentist D must observe such deviated images for a long time, the dentist D will feel eye fatigue to cause, for example, a headache. The embodiment of the present invention solves this problem by photographing left- and right-eye images of the treatment target T with the single photographing element 31.

In summary, the embodiment of the present invention supports the photographing unit and stereoscopic display unit with the first and second auxiliary arms that are supported with the support arm of the stand. The stand allows the photographing unit and stereoscopic display unit together to be widely moved and the first and second auxiliary arms allow them to be freely oriented. The embodiment, therefore, is appropriate for dental treatment and is capable of reducing fatigue of a dentist during treatment.

According to the embodiment, the first and second auxiliary arms each have two parallel sub-linkages connected to each other through a joint serving as an angular position transformer of link element. This configuration is simple to move the photographing unit and other units to required positions. Front ends of the first and second auxiliary arms rotatably support the photographing unit and stereoscopic display unit, respectively, so that the user can freely move the units to required positions and adjust directions of the units at the positions.

According to the embodiment, the front link to which the first and second auxiliary arms are attached keeps a vertical state when the support arm is turned in a vertical direction or when the parallel sub-linkages are together turned in a horizontal direction. Accordingly, the photographing unit and stereoscopic display unit can be translated in vertical and horizontal directions without changing the posture and relative positions thereof, to allow the user to conduct comfortable observation. Since the front link is always vertical, total balance is always maintained with the counterweight without readjustment even when the first and second auxiliary arms are moved to change distances from the front link to the photographing unit and stereoscopic display unit. Namely, the photographing unit and stereoscopic display unit are movable without destabilizing the balanced state of the stand.

According to the embodiment, the photographing unit and stereoscopic display unit are supported with the first and second auxiliary arms that are supported with the support arm of the stand. The stand allows the photographing unit and stereoscopic display unit together to be widely moved. Inclination angles of the links of the first and second auxiliary arms relative to the stand body are fixable to fix reference angles of the photographing unit and stereoscopic display unit. Accordingly, the photographing unit and stereoscopic display unit can easily be kept in given directions or changed to optional directions. The embodiment, therefore, is appropriate for dental treatment and allows a dentist to comfortably conduct dental treatment.

According to the embodiment, the fifth and sixth parallel sub-linkages of the second auxiliary arm receive resiliency to restrict free deformation, so that the second auxiliary arm is easy to manipulate.

Although the invention has been described above by reference to certain embodiments of the invention, the invention is not limited to the embodiments described above. Modifications and variations of the embodiments described above will occur to those skilled in the art, in light of the teachings. The scope of the invention is defined with reference to the following claims.

What is claimed is:
1. A dental treatment observation system comprising:
a stand including a parallel linkage provided with first and second parallel sub-linkages,
the parallel linkage having first and second link elements that face each other and third and fourth link elements that face each other, the first link element being rotatably fixed at a stand body, the fourth link element supporting a counterweight, a support arm being fixed to the third link element, and a front link rotatably fixed at the support arm,
the first parallel sub-linkage having fifth and sixth link elements that face each other and seventh and eighth link elements that face each other, the fifth link element being fixed relative to the first link element, the eighth link element being positionally fixed to the stand body,
the second parallel sub-linkage defined by four link elements including ninth and tenth link elements that face each other, the ninth link elements being fixed relative to the seventh link elements, the tenth link elements being positionally fixed to the front link;
a first auxiliary arm attached to the front link and configured to movably and rotatably support a photographing unit that stereoscopically photographs an object and provides a pair of left and right images of the object having a binocular parallax, the first auxiliary arm including third and fourth parallel sub-linkages,
the third parallel sub-linkage having four link elements including eleventh and twelfth link elements that face each other, the eleventh link element being positionally fixed to the front link, the fourth parallel sub-linkage having four links including thirteenth and fourteenth link elements that face each other, the thirteenth link elements being positionally fixed to the twelfth link element, the photographing unit being positionally fixed to the fourteenth link; and a second auxiliary arm attached to the front link and configured to movably and rotatably support a stereoscopic display unit that displays the pair of left and right images on internal display panels so that the images are stereoscopically observed through a pair of eyepieces, the second auxiliary arm including fifth and sixth parallel sub-linkages, the fifth parallel sub-linkage having four link elements including fifteenth and sixteenth link elements that face each other, the fifteenth link element being positionally fixed to the front link, the sixth parallel sub-linkage having four link elements including seventeenth and eighteenth link elements that face each other, the seventeenth link element being fixed relative to the sixteenth link element, the stereoscopic display unit being positionally fixed to the eighteenth link element.

2. The dental treatment observation system of claim 1, further comprising:
  a clutch configured to fix adjacent ones of the link elements of the third parallel sub-linkage; and
  a clutch configured to fix adjacent ones of the link elements of the fourth parallel sub-linkage.

3. The dental treatment observation system of claim 1, wherein:
  adjacent ones of the links of the fifth parallel sub-linkage are resiliently pushed to each other; and
  adjacent ones of the links of the sixth parallel sub-linkage are resiliently pushed to each other.

4. The dental treatment observation system of claim 1, wherein
  the photographing unit has a single two-dimensional photographing element to simultaneously photograph a pair of left and right images of the object.

5. The dental treatment observation system of claim 1, further comprising
  a third auxiliary arm attached to the support arm and configured to support a dental treatment tool.

* * * * *